US00PP33948P2

(12) United States Plant Patent
Müller

(10) Patent No.: US PP33,948 P2
(45) Date of Patent: Feb. 8, 2022

(54) ***PETUNIA* PLANT NAMED 'KLEPH20522'**

(50) Latin Name: *Petunia hybrida*
Varietal Denomination: KLEPH20522

(71) Applicant: Klemm+Sohn GmbH & Co. KG, Stuttgart (DE)

(72) Inventor: Leonhard Müller, Rott am Inn (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/362,545

(22) Filed: Jun. 29, 2021

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05)

(58) Field of Classification Search
USPC ..... Plt./356.13
CPC ..... A01H 6/824; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Petunia* plant particularly distinguished by being a medium-vigorous plant with a semi-upright habit and having apricot-colored flowers, is disclosed.

1 Drawing Sheet

Genus and species: *Petunia hybrida.*
Variety denomination: 'KLEPH20522'.

BACKGROUND OF THE NEW PLANT

The present invention comprises a new and distinct variety of *Petunia*, botanically known as *Petunia hybrida*, and hereinafter referred to by the variety name 'KLEPH20522'. 'KLEPH20522' originated from a cross-pollination conducted in April 2016 in Rott am Inn, Germany between the proprietary female *Petunia* variety '15G24' (unpatented) and the proprietary male *Petunia* variety '15G31' (unpatented).

The seeds from the cross were sown and plants were grown in a greenhouse for evaluation, where an individual plant designated 'KLEPH20522' was selected from the group of plants in April 2017 in Rott am Inn, Germany. In May 2017, 'KLEPH20522' was first vegetatively propagated by terminal tip cuttings and tissue culture in Rott am Inn, Germany. 'KLEPH20522' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. A medium-vigorous plant with a semi-upright habit; and
2. Apricot-colored flowers.

DESCRIPTION OF THE PHOTOGRAPH

This new *Petunia* plant is illustrated by the accompanying photograph of a plant grown outdoors in Stuttgart, Germany in June 2020. The photograph shows the foliage and flowers of a 4-month-old plant grown in a pot. The colors shown are as true as can be reasonably obtained by conventional photographic procedures.

DESCRIPTION OF THE NEW VARIETY

The following detailed descriptions set forth the distinctive characteristics of 'KLEPH20522'. The data which define these characteristics were collected from asexual reproductions carried out in Latina, Italy. Data was collected on plants grown 14-weeks from cultivation from potting in a glass greenhouse in Latina, Italy in March 2021. Color references are to The R.H.S. Colour Chart of The Royal Horticultural Society of London (R.H.S.), 5$^{th}$ edition (2007).

Classification:
- *Family.*—Solanaceae.
- *Botanical.*—*Petunia hybrida.*
- *Common.*—*Petunia.*
- *Designation.*—'KLEPH20522'.

Parentage:
- *Female parent.*—The proprietary female *Petunia* variety '15G24' (unpatented).
- *Male parent.*—The proprietary male *Petunia* variety '15G31' (unpatented).

Plant:
- *Vigor.*—Medium vigor.
- *Habit.*—Semi-upright.
- *Height (from top of soil).*—27.0 cm.
- *Width (horizontal plant diameter).*—70.0 cm.
- *Propagation.*—Terminal tip cuttings and tissue culture.
- *Time to produce a finished flowering plant.*—About 14 weeks in the winter under short day conditions, and 7 weeks in the spring.
- *Time to initiate and develop roots.*—2 to 3 weeks.
- *Root description.*—Moderate density, moderate branching, white roots.

Stems:

*Average number* (*basal*).—7.

*Length of basal branches* (*from the base of the stem to the tip*).—40.0 cm.

*Internode length*.—2.5 cm.

*Diameter of branches* (*from midpoint*).—0.3 cm.

*Stem color*.—RHS 144A (Yellow-Green).

*Anthocyanin*.—Absent.

*Texture*.—Pubescent.

Leaves:

*Arrangement*.—Alternate along the stem and opposite under the inflorescence.

*Length*.—4.5 cm.

*Width*.—2.0 cm.

*Shape*.—Elliptic.

*Apex*.—Acute.

*Base*.—Attenuate.

*Margin*.—Entire.

*Immature leaf color*.—Upper surface: RHS 137B (Green). Lower surface: RHS 138A (Green).

*Mature leaf color*.—Upper surface: RHS N137A (Green). Lower surface: RHS 137C (Green).

*Texture* (*both upper and lower surfaces*).—Pubescent.

*Venation pattern*.—Arcuate.

*Venation color*.—Upper surface: RHS N137A (Green). Lower surface: RHS 137C (Green).

*Petioles*.—Length: 0.3 cm. Diameter: 0.3 cm. Color: RHS 138B (Green). Texture: Pubescent.

Flower buds:

*Shape*.—Irregular oblong.

*Length*.—5.5 cm.

*Diameter*.—0.6 cm.

*Color at tight bud*.—RHS 145A (Yellow-Green).

*Texture*.—Pubescent.

Inflorescence:

*Blooming habit* (*flowering season*).—Continuously flowering during spring and summer.

*Inflorescence type*.—Sympodial, with monochasial growth.

*Number of flowers per node*.—1.

*Lastingness of individual blooms on the plant*.—About 10 days.

*Fragrance*.—Absent.

*Flowers*.—Arrangement: Composed of 5 petals fused at the base. Diameter (flower face): 7.0 cm. Depth (total length of flower): 7.0 cm. Throat/Funnel: Length: 3.7 cm. Diameter (at opening): 1.0 cm. Texture: Inner surface: Smooth. Outer surface: Pubescent. Color: Inner surface: RHS 153C (Yellow-Green). Outer surface: RHS N144D (Yellow-Green). Petals: Color of petals, mature flower (fully opened): Upper surface: N163D (Greyed-Orange) is the main color. Lower surface: RHS 160A (Greyed-Yellow). Apex: Cuspidate. Base: Fused. Shape: Salverform. Margin: Entire. Strength of waviness: Medium. Degree of lobation: Medium. Calyx arrangement: Actinomorphic, composed of 5 sepals fused at the base. Sepals: Color: Upper surface: RHS 137B (Green). Lower surface: RHS 137B (Green). Length: About 1.8 cm. Width: 0.2 cm. Shape: Linear. Apex: Acute. Base: Attenuate. Margin: Entire. Texture (both upper and lower surfaces): Pubescent.

*Pedicels*.—Color: RHS 144A (Yellow-Green). Length: 4.5 cm. Diameter: 0.15 cm. Texture: Pubescent.

Reproductive organs:

*Stamens*.—Quantity: 5. Shape: Needle with oblong head. Filament: Length: 1.7 cm. Diameter: 0.01 cm. Color: RHS 145C (Yellow-Green). Anther: Shape: Oblong. Color: RHS 160B (Greyed-Yellow). Length: 0.3 cm. Diameter: 0.25 cm. Pollen: Color: RHS 158B (Yellow-White). Amount: Moderate.

*Pistils*.—Quantity per flower: 1. Length: 2.9 cm. Stigma color: RHS 143A (Green). Style color: RHS 144D (Yellow-Green).

Fruit and seed set: No fruit and seed set observed to date.

Disease and pest/insect resistance: No disease and pest/insect resistance observed.

COMPARISON WITH PARENTAL LINES AND KNOWN VARIETY

'KLEPH20522' is a distinct variety of *Petunia* and is distinguished from its parents as described in Table 1.

TABLE 1

Comparison with Parental Lines

| Characteristic | 'KLEPH20522' | Female Parent '15G24' | Male Parent '15G31' |
|---|---|---|---|
| Flower color | Apricot | Yellow | Yellow |

'KLEPH20522' is a distinct variety of *Petunia* and differences between CASCADIAS 'Indian Summer' (patent status unknown) are described in Table 2.

TABLE 2

Comparison with Similar Variety

| Characteristic | 'KLEPH20522' | CASCADIAS 'Indian Summer' |
|---|---|---|
| Flower size | Bigger than CASCADIAS 'Indian Summer' | Smaller than 'KLEPH20522' |

I claim:

1. A new and distinct variety of *Petunia* plant designated 'KLEPH20522' as illustrated and described herein.

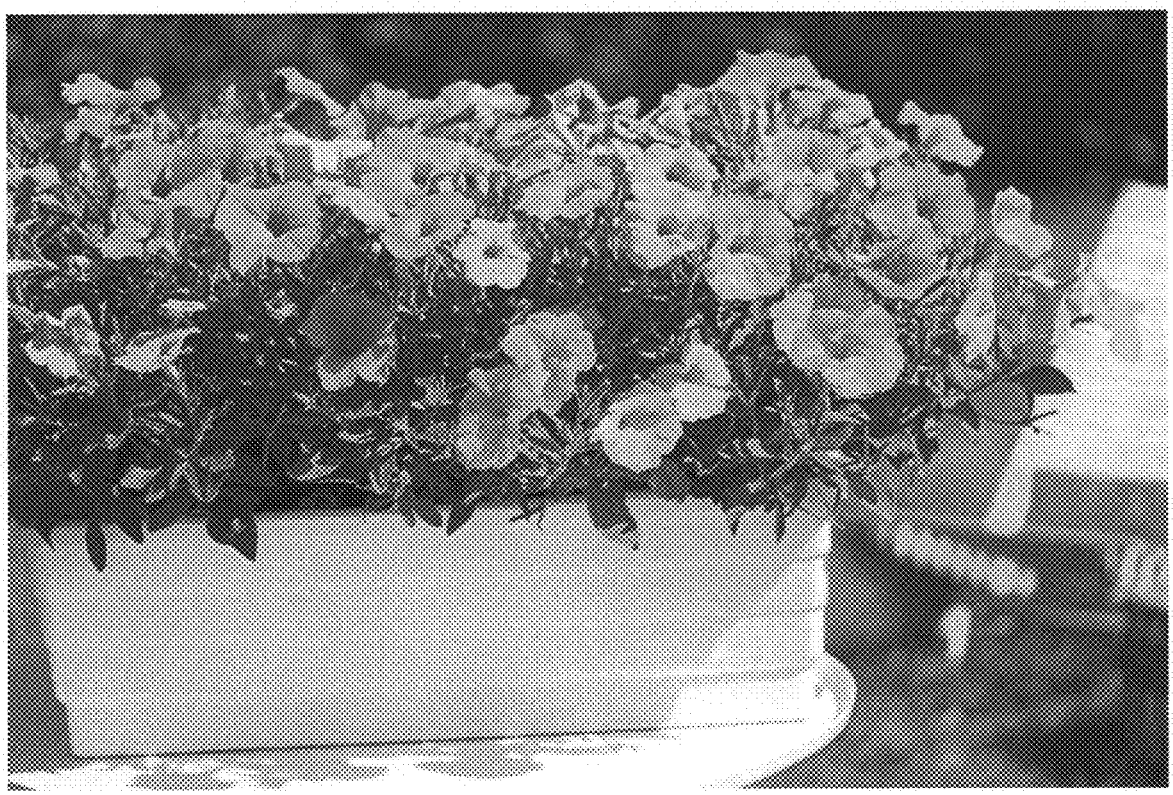

* * * * *